United States Patent [19]

Chang et al.

[11] 4,380,669

[45] Apr. 19, 1983

[54] PROCESS FOR SYNTHESIZING ANILINE

[75] Inventors: Clarence D. Chang, Princeton; William H. Lang, Pennington, both of N.J.

[73] Assignee: Mobil Oil Corporation, New York, N.Y.

[21] Appl. No.: 252,487

[22] Filed: Apr. 8, 1981

[51] Int. Cl.³ ............................................... C07C 85/06
[52] U.S. Cl. ..................................... 564/402; 564/403
[58] Field of Search ................ 564/402, 403, 474, 479

[56] References Cited

U.S. PATENT DOCUMENTS

| | | | |
|---|---|---|---|
| 2,331,600 | 1/1966 | Jones et al. | 260/465 |
| 3,231,616 | 1/1966 | Jones | 260/581 |
| 3,272,865 | 9/1966 | Barker | 564/402 |
| 3,384,667 | 5/1968 | Hamilton | 564/402 X |
| 4,082,805 | 4/1978 | Kaeding | 564/474 |

FOREIGN PATENT DOCUMENTS

| | | | |
|---|---|---|---|
| 2516316 | 10/1976 | Fed. Rep. of Germany | 564/402 |
| 49-29176 | 8/1974 | Japan | 564/402 |

OTHER PUBLICATIONS

Yakabe et al., "Chemical Abstracts", vol. 88, Abstract No. 39423g, (1978).

*Primary Examiner*—John Doll
*Attorney, Agent, or Firm*—Charles A. Huggett; Michael G. Gilman; Malcolm D. Keen

[57] ABSTRACT

A process for converting phenolic compounds to aniline by passing them over ammonia in the presence of ZSM-5 type zeolites under conversion conditions whereby high conversion, high selectivity and improved rates of production are achieved.

8 Claims, No Drawings

PROCESS FOR SYNTHESIZING ANILINE

BACKGROUND OF THE INVENTION

1. Field of the Invention

This invention is directed to an improved process wherein aniline is synthesized from phenol over ammonia.

2. Description of the Prior Art

Aniline is an important organic chemical. Many highly useful products can be produced from it. Aniline is the simplest of the primary aromatic amines. Aniline and other aromatic amines can be prepared by several prior art methods, one, for example, is the reduction of nitro compounds obtained by direct nitration of the benzene ring. Important derivatives of aniline include toluidines, xylidenes, n-alkyl, n-aryl and n-acyl derivatives.

Aniline was first produced in 1826 by dry distillation of indigo. Traditionally, it has been prepared by nitrating benzene, then reducing the nitrobenzene with iron and hydrochloric acid such as in the reduction of nitrobenzene with iron filings or borings and 30 percent hydrochloric acid; catalytic reaction of chlorobenzene with aqueous ammonia in the vapor phase and the reduction of nitrobenzene with hydrogen. Also a catalytic ($Al_2O_3$) process is known wherein the organic amines are obtained by ammoniation of phenolic-type compounds; U.S. Pat. No. 3,860,650. Additionally, phenol can also be subjected to gas phase ammonolysis with the Halcon-Scientific Design process. This process employs high temperatures and high pressures and is catalyzed by catalysts such as alumina-silica and mixtures of manganese-boron oxides and alumina-titania or are combined with additional co-catalysts such as cerium, vanadium or tungsten. Although selectivity in such processes is as high as 90 percent, highly undesirable by-products such as diphenylamine and carbazole are produced. U.S. Pat. No. 3,272,865 is drawn to a method of obtaining high yields of aromatic amines from hydroxybenzenes by catalytic exchange of the hydroxyl group for the amino group in the presence of ammonia. It is also of interest in that it uses silica-alumina, titanium-alumina, zirconia-alumina catalysts plus phosphoric acid and tungsten oxide apparently as co-catalysts.

SUMMARY OF THE INVENTION

In accordance with the present invention, phenol and phenolic-type compounds may be converted to aniline by passing ammonia or suitable amines over ZSM-5 type zeolite catalysts. The process is highlighted by good selectivity to aniline with only minor amounts of undesirable by-products.

DESCRIPTION OF PREFERRED EMBODIMENTS

The phenols in accordance with the present invention may be aminated with ammonia or other suitable amino-type compounds. In this process, by-products such as diphenylamine and carbazole are suppressed or eliminated through use of ZSM-5-type zeolites, by virtue of their shape selectivity. Phenol or any other suitable phenolic compound may be used in accordance with the present invention to produce aniline or substituted anilines such as 2,4,6-tribromoaniline, iodaniline, n-methylaniline or p-toluidine. Ammonia or other suitable amine may be used to convert the phenol to aniline and N-substituted anilines. Suitable amines include primary alkyl amines as methylene, ethylamine, etc., and also such alkyl amines as tertiary-butyl amine.

Process parameters may vary from about 400° to about 1200° F., from about 1–250 atmospheres and from about 0.5 to about 50 LHSV. The phenolic-type compounds and ammonia or a suitable amine may be reacted directly over the ZSM-5 type catalyst, or a suitable solvent such as benzene may be used.

The zeolite catalysts utilized herein are members of a novel class of zeolites exhibiting some unusual properties. The zeolites induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperatures which induces irreversible collapse of the framework for other zeolites, e.g., of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render the zeolites ineffective.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10 percent and 60 percent. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
| --- | --- |
| ZSM-5 | 8.3 |
| ZSM-11 | 8.7 |
| ZSM-12 | 2 |
| ZSM-38 | 3 |
| ZSM-35 | 4.5 |
| TMA Offretite | 3.7 |
| Beta | 0.6 |
| ZSM-4 | 0.5 |
| H—Zeolon | 0.4 |
| REY | 0.4 |
| Amorphous Silica-Alumina | 0.6 |
| Erionite | 38 |

It is to be realized that the above constraint index values typically characterize the specified zeolites bu that such are the cumulative result of several variables used in determination and calculation thereof. Thus, for a given zeolite depending on the temperature employed within the aforenoted range of 550° F. to 950° F., with accompanying conversion between 10 percent and 60 percent, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. Pat. No. 4,046,859, which is incorporated herein by reference. This zeolite is, in one aspect, identified in the patent in terms of mole ratios of oxides and in the anhydrous state, as follows:

$$(0.3-2.5)R_2O:(0-0.8)M_2O:Al_2O_3:>8SiO_2$$

wherein R is an organic nitrogen-containing cation derived from a 2-(hydroxyalkyl) trialkylammonium compound and M is an alkali metal cation, and is characterized by a specified X-ray pwder diffraction pattern.

In a preferred synthesized form, the zeolite has a formula, in terms of mole ratios of oxides and in the anhydrous state, as follows:

$$(0.4-2.5)R_2O:(0-0.6)M_2O:Al_2O_3:>xSiO_2$$

wherein R is an organic nitrogen-containing cation derived from a 2-hydroxyalkyl) trialkylammonium compound, wherein alkyl is methyl, ethyl or a combination thereof, M is an alkali metal, especially sodium, and x is from greater than 8 to about 50.

The synthetic ZSM-38 zeolite possess a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33 Å.

TABLE I

| d (A) | I/Io |
| --- | --- |
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |

TABLE I-continued

| d (A) | I/Io |
|---|---|
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio of n-hexane/2-methylpentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| $R^+$ | Broad | Preferred |
|---|---|---|
| $\frac{R^+}{R^+ + M^+}$ | 0.2–1.0 | 0.3–0.9 |
| $OH^-/SiO_2$ | 0.05–0.5 | 0.07–0.49 |
| $H_2O/OH^-$ | 41–500 | 100–250 |
| $SiO_2/Al_2O_3$ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. Pat. No. 4,016,245, all of which is incorporated herein by reference. This zeolite is, in one aspect, identified in the patent in terms of mole ratios of oxides and in the anhydrous state, as follows:

(0.3–2.5)$R_2O$:(0–0.8)$M_2O$:$Al_2O_3$:>8$SiO_2$ wherein R is an organic nitrogen-containing cation derived from ethylenediamine or pyrrolidine and M is an alkali metal cation, and is characterized by a specified X-ray powder diffraction pattern.

In a preferred synthesized form the zeolite has a formula, in terms of mole ratios of oxides and in the anhydrous state, as follows:

(0.4–2.5)$R_2O$:(0–0.6)$M_2O$:$Al_2O_3$:$xSiO_2$ wherein R is an organic nitrogen-containing cation derived from ethylenediamine or pyrrolidine, M is an alkali metal, especially sodium, and x is from greater than 8 to about 50.

The synthetic ZSM-35 zeolite possess a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33 Å. Close examination of some individual samples of ZSM-5 may show a very weak line at 11.3–11.5 Å. This very weak line, however, is determined not to be a significant line for ZSM-35.

TABLE II

| d (A) | I/Io |
|---|---|
| 9.6 ± 0.2 | Very Strong ± Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| $R^+ + M^+$ | 0.2–1.0 | 0.3–0.9 |
| $OH^-/SiO_2$ | 0.05–0.5 | 0.07–0.49 |
| $H_2O/OH^-$ | 41–500 | 100–250 |
| $SiO_2/Al_2O_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g., at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes by converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | .28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.55 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal from, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent weight of the composite. Indications are that the catalyst will show very slow aging in this configuration.

The following examples are meant in no way to limit the invention.

EXAMPLE 1

Phenol (94 g) and $NH_3$ (34 g) were reacted over HZSM-5 at 950° F., 5.3 atm., and 1 LHSV. The conversion of phenol was 70 percent. The products consisted of aniline with only slight traces of diphenylamine, less than 3 percent of other products and no detectable carbazole.

It is clear from these data that the process of the present invention produces an essentially pure product and that unwanted by-products are suppressed or substantially eliminated.

EXAMPLE II

A charge stock comprising 75 percent phenol in benzene was fed (4 cc/hr.) along with liquid $NH_3$ (7.5 cc/hr.) over 6 cc of the zeolite H-mordenite at 950° F. and 400 psig. The conversion of phenol was 96 percent in the first half hour, but dropped to 75 percent after 1½ hours. Product selectivities are compared with results from HZSM-5 under similar reaction conditions in the following table:

|  | HZSM-5 | H—Mordenite | |
|---|---|---|---|
| Time on stream, hr. | 8 | 0.5 | 1.5 |
| Conversion, wt. percent | 92.4 | 96.0 | 74.9 |
| Selectivity, wt. percent |  |  |  |
| Aniline | 99.6 | 95.8 | 99.2 |
| Diphenylamine | 0.2 | 0.6 | 0.2 |
| Carbazole | 0.1 | 0.5 | 0.3 |
| Tars, etc. | 0.1 | 3.1 | 0.3 |
|  | 100.0 | 100.0 | 100.0 |

It is clear from the data of this example that HZSM-5 is much more stable toward aging than H-mordenite, and that at high conversions HZSM-5 shows superior selectivity.

We claim:

1. A process for converting phenol or phenolic type compounds to aniline or substituted anilines comprising contacting said phenol or phenolic compound with ammonia or a suitable amine under conversion conditions in the presence of a crystalline alumino silicate zeolite having a constraint index within the approximate range of 1–12 and a silica to alumina ratio of at least 12.

2. The process of claim 1 wherein the phenolic compound is converted to aniline by contacting it with ammonia.

3. The process of claim 2 wherein the conversion conditions are as follows:
Temperature—about 400°–1200° F.;
Pressure—about 1–250 atmospheres;
Reaction Time—LHSV from about 0.5–50.

4. The process of claim 1, 2 or 3 wherein the crystalline aluminosilicate is a ZSM-5 type zeolite selected from the group consisting of ZSM-5, ZSM-11, ZSM-12, ZSM-38, ZSM-35 wherein in said zeolites may be base exchanged, contain metal cations or be acidic in nature.

5. The process of claim 4 wherein the zeolite is ZSM-5.

6. The process of claim 4 wherein the zeolite is H-ZSM-5.

7. The process of claim 4 wherein the zeolite is ZSM-11.

8. The process of claim 4 wherein the zeolite is H-ZSM-11.

* * * * *